(12) United States Patent
Thomasco et al.

(10) Patent No.: US 6,875,871 B2
(45) Date of Patent: Apr. 5, 2005

(54) OXAZOLIDINONE PHOTOAFFINITY PROBES

(75) Inventors: Lisa Marie Thomasco, Kalamazoo, MI (US); Robert C. Gadwood, Kalamazoo, MI (US)

(73) Assignee: Pharmacia & Upjohn Company, Kalamazoo, MI (US)

(*) Notice: Subject to any disclaimer, the term of this patent is extended or adjusted under 35 U.S.C. 154(b) by 99 days.

(21) Appl. No.: 10/359,767

(22) Filed: Feb. 6, 2003

(65) Prior Publication Data

US 2003/0232008 A1 Dec. 18, 2003

Related U.S. Application Data

(62) Division of application No. 09/738,022, filed on Dec. 15, 2000, now abandoned.

(51) Int. Cl.[7] .............................................. C07D 413/10
(52) U.S. Cl. .................................. 546/271.4; 546/272.1
(58) Field of Search ........................... 546/271.4, 272.1

(56) References Cited

U.S. PATENT DOCUMENTS 5,652,238 A    7/1997   Brickner et al.
5,910,504 A    6/1999   Hutchinson

FOREIGN PATENT DOCUMENTS

| WO | WO93/09103 | 5/1993 |
| WO | WO95/14684 | 6/1995 |
| WO | WO99/41244 | 8/1999 |
| WO | WO00/10566 | 3/2000 |
| WO | WO01/94342 | 12/2001 |

OTHER PUBLICATIONS

Matassova, et al., "Ribosomal RNA is the target for oxazolidinones, a novel class of translation inhibitors," RNA (1999) 5:939–946.

Porse et al, "Direct crosslinking of the antitumorantibiotic sparsomycin, and its derivatives, to A2602 in peptidyl transferase center of 23S–like rRNA within tRNA complexes," Proc. Natl. Acad. Sci. USA (1999) 96:9003–9008.

*Primary Examiner*—Patricia L. Morris
(74) *Attorney, Agent, or Firm*—Lucy X. Yang

(57) ABSTRACT

Disclosed are novel compounds that are useful and effective as photoaffinity probes and methods of using oxazolidinone photoaffinity probes.

5 Claims, No Drawings

OXAZOLIDINONE PHOTOAFFINITY PROBES

CROSS-REFERENCE TO RELATED APPLICATIONS

This application is a divisional of U.S. Ser. No. 09/738,022 filed Dec. 15, 2000, now abandoned which is incorporated herein by reference in its entirety.

FIELD OF THE INVENTION

The present invention is directed, in part, to novel photolabile oxazolidinones and preparation thereof. The novel compounds can be used as photoaffinity probes within sensitive bacteria including both gram-positive and gram-negative bacteria and mammalian cells.

BACKGROUND OF THE INVENTION

A number of antibiotic compounds have been developed and shown to be effective in inhibiting translation. The antibiotics neomycin, thiostrepton, and hygromycin appear to inhibit translocation and occupation of the A site within a ribosome but have no effect on formation of the fMet-tRNA$_f^{Met}$/ribosome translation complex nor on the peptide-bond synthesis which occurs in the absence of elongation factor P. Streptomycin, which causes misreading and also inhibits A-site binding, interacts with two sites on the 16S rRNA of the 30S subunit. Lincomycin inhibits peptidyltransferase and occupation of the A-site. Erythromycin inhibits peptidyltransferase and destabilizes the peptidyl-tRNA/ribosome/mRNA complex.

A number of additional compounds have been recently developed and have been shown to act as antimicrobial or antibacterial agents. International Publication WO 99/41244 discloses substituted aminophenyl isoxazoline compounds useful as antimicrobial agents. U.S. Pat. No. 5,910,504 describes hetero-aromatic ring substituted phenyloxazolidinone antimicrobial agents. In addition, International Publication WO 00/10566 discloses isoxazolinone antibacterial agents. An important step in the development of new antimicrobial or antibacterial agents, such as those disclosed above, is the elucidation of a mechanism of action. The specific site of interaction of non selective antibiotics/antitumor agents, such as sparsomycin, that inhibit protein translation by a different, less useful, and direct mechanism, has been described. Porse et al., *Proc. Natl. Acad. Sci. USA*, 1999, 96, 9003–9008. Previous studies with chemical probes using isolated, cell-free systems have failed to define the relative sites of interaction of these types of antibiotic compounds of the oxazolidinone class. Matassova, et al., *RNA*, 1999, 5, 939–946. This is, in part, because the previous methods were incapable of defining the sites of the particular and specific mechanism of action of this important class of antibiotics. Probes that help to elucidate the mechanism of action of antimicrobial and/or antibacterial agents and methods of using the same are highly desired.

The present invention is directed, inter alia, to novel oxazolidinone compounds and use of oxazolidinone compounds as photoaffinity probes. Compounds suspected of having antimicrobial and/or antibacterial activity can be used in intact cells and can be evaluated for a mechanism of action by using active and inactive enantiomers of oxazolidinone compounds as competitors for crosslinking to components within the cell. The compounds and methods of the present invention allow one skilled in the art to elucidate the mechanism of action of antibacterial and/or antimicrobial agents that are suspected of inhibiting protein translation. These and other aspects of the invention are described below.

SUMMARY OF THE INVENTION

The present invention is directed to novel compounds that are useful and effective as photoaffinity probes useful for, inter alia, identification of the oxazolidinone binding site within gram-positive and gram-negative bacteria. These compounds can also be used for aiding in the determination of oxazolidinone binding sites within mammalian cells.

The compounds of the present invention comprise Formula I shown below.

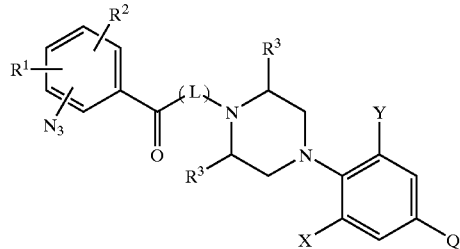

Formula I wherein X and Y are, independently, F, H or CH$_3$; R$^1$ is H or I; R$^2$ is H or OH; R$^3$ is H or C$_1$–C$_8$ alkyl; L is a bond or —OCH$_2$C(=O); and Q is

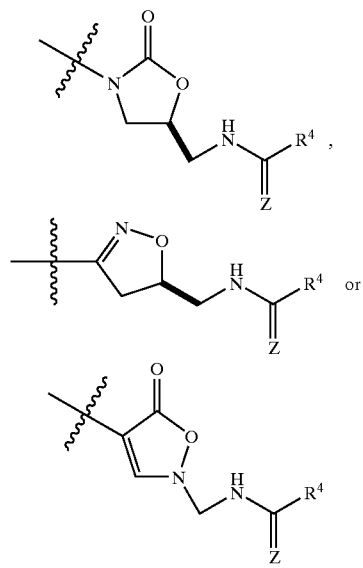

wherein R$^4$ is H, CH$_3$, CH$_2$CH$_3$ or cyclopropyl; and Z is O or S; or a pharmaceutically acceptable salt thereof.

Other compounds of the present invention comprise Formula II shown below.

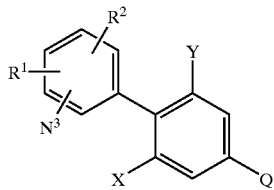

Formula II wherein X and Y are, independently, F, H or CH$_3$; R$^1$ is H or I; R$^2$ is H or OH; and Q is

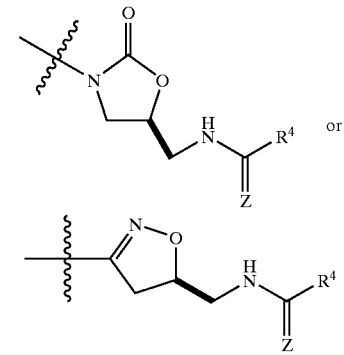

wherein R$^4$ is H, CH$_3$, CH$_2$CH$_3$ or cyclopropyl; and Z is O or S; or a pharmaceutically acceptable salt thereof.

Other compounds of the present invention comprise Formula III shown below.

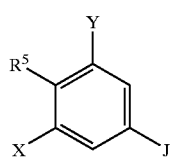

wherein X and Y are, independently, F, H or CH$_3$; R$^5$ is

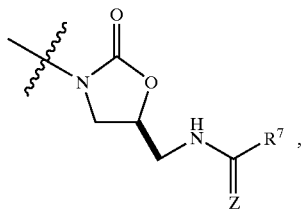

wherein R$^6$ is H, N$_3$, halogen, NH$_2$, OH, SH, C$_1$–C$_4$ alkylamino, C$_1$–C$_4$ dialkylamino, C$_1$–C$_4$ alkyl, nitrile, carboxamide, C$_1$–C$_4$ alkoxy, C$_1$–C$_4$ alkylthio, or C$_1$–C$_4$ alkoxycarbony; and J is

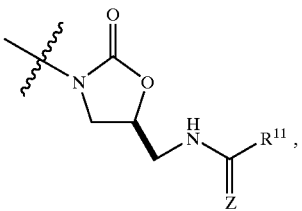

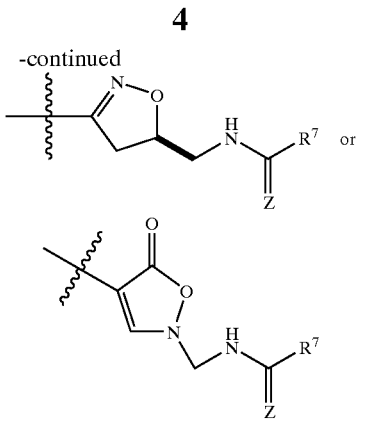

wherein Z is O or S; and R$^7$ is

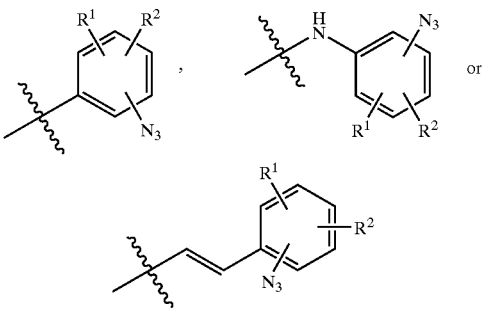

wherein R$^1$ is H or I; and R$^2$ is H or OH; or a pharmaceutically acceptable salt thereof.

In other embodiments of the invention, methods of using a compound comprising Formula IV as a photoaffinity probe are provided, wherein Formula IV is Formula IV

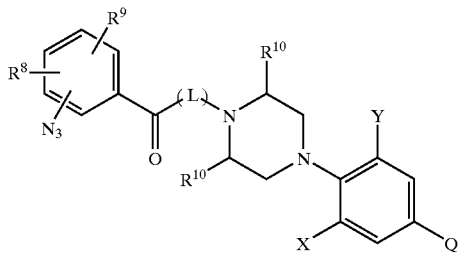

wherein X and Y are, independently, F, H or CH$_3$; R$^8$ is H or I; R$^9$ is H or OH; R$^{10}$ is H or C$_1$–C$_8$ alkyl; L is a bond or —OCH$_2$C(=O); and Q is

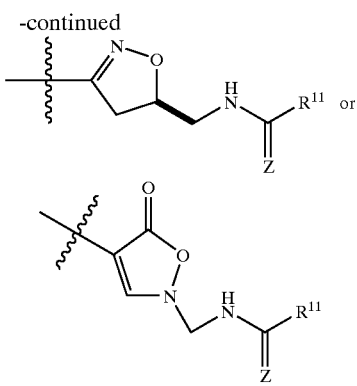

wherein $R^{11}$ is H, $CH_3$, $CH_2CH_3$ or cyclopropyl; and Z is O or S; or a pharmaceutically acceptable salt thereof.

In other embodiments of the invention, methods of using a compound comprising Formula V as a photoaffinity probe are provided, wherein Formula V is Formula V

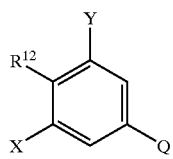

wherein X and Y are, independently, F, H or $CH_3$; $R^{12}$ is $N_3$ or

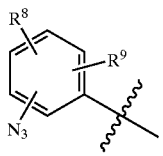

wherein $R^8$ is H or I; $R^9$ is H or OH; and Q is

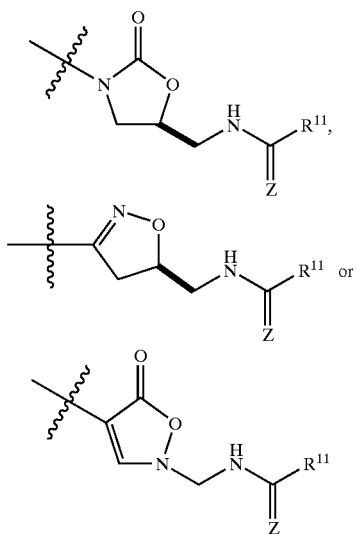

wherein $R^{11}$ is H, $CH_3$, $CH_2CH_3$ or cyclopropyl; and Z is O or S; or a pharmaceutically acceptable salt thereof.

In other embodiments of the invention, methods of using a compound comprising Formula VI as a photoaffinity probe are provided, wherein Formula VI is Formula VI

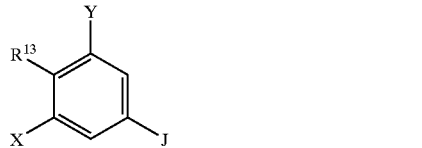

wherein X and Y are, independently, F, H or $CH_3$; $R^{13}$ is

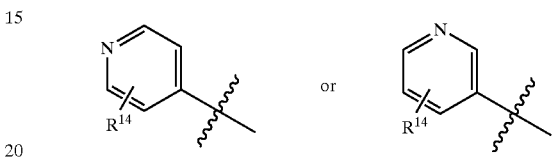

wherein $R^{14}$ is H, $N_3$, halogen, $NH_2$, OH, SH, $C_1$–$C_4$ alkylamino, $C_1$–$C_4$ dialkylamino, $C_1$–$C_4$ alkyl, nitrile, carboxamide, $C_1$–$C_4$ alkoxy, $C_1$–$C_4$ alkylthio, or $C_1$–$C_4$ alkoxycarbonyl; and J is

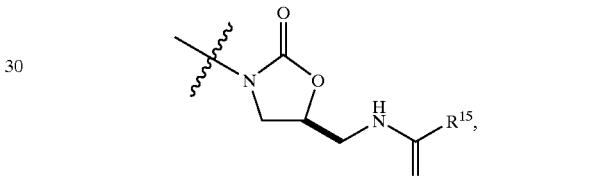

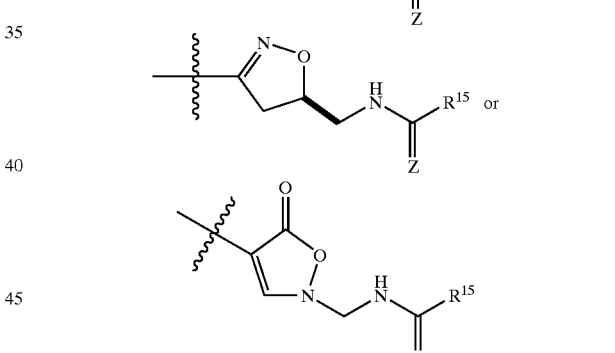

wherein: Z is O or S; and $R^{15}$ is

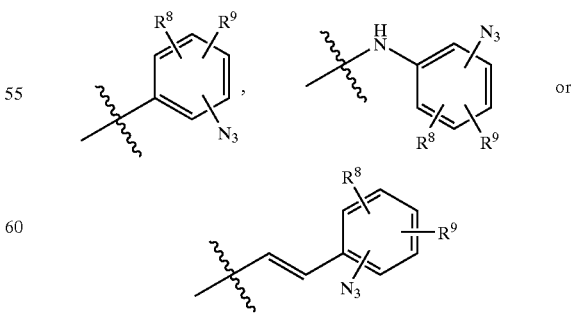

wherein $R^8$ is H or I; and $R^9$ is H or OH; or a pharmaceutically acceptable salt thereof.

DETAILED DESCRIPTION OF PREFERRED EMBODIMENTS

Various definitions are made throughout this document. Most words have the meaning that would be attributed to those words by one skilled in the art. Words specifically defined either below or elsewhere in this document have the meaning provided in the context of invention as a whole and as are typically understood by those skilled in the art.

As used herein, the term "cross-linking" or "binding" means the physical interaction between the photoaffinity probe and at least one component within a cell or from a cell or combinations thereof. Binding includes ionic, non-ionic, Hydrogen bonds, Van der Waals, hydrophobic interactions, etc. The physical interaction, the binding, can be either direct or indirect, indirect being through or because of another protein or compound. Direct binding refers to interactions that do not take place through or because of another protein or compound but instead are without other substantial chemical intermediates.

As used herein, the term "component" within a cell means any protein, nucleic acid, lipid, etc. within a cell. Components include, but are not limited to, the contents of the cytoplasm, nucleus, cell membrane, cell wall, and the like.

As used herein, the term "competitor compound" means any identifiable chemical or molecule, small molecule, peptide, protein, sugar, natural or synthetic, that is suspected (such as a test compound) to potentially interact with or compete with the photoaffinity probe for cross-linking to a component within a cell or from a cell.

As used herein, the term "contacting" means either direct or indirect, application of a photoaffinity compound or competitor compound within a cell, on or to a cell, or to components from a cell. The competitor compound or photoaffinity compound can be present within a buffer, salt, solution, etc.

As used herein, the term "oxazolidinone" means a compound of the class known as oxazolidinones, including the compounds described in U.S. Ser. Nos. 07/438,759, 07/553, 795, 08/006,596, 07/882,407, 07/786,107, 07/831,213, 08/233,903, 08/119,279, 08/226,158, 08/155,988, 08/329, 717, 07/909,387, 08/339,979, 08/384,278, 08/875,800, 07/880,432, 08/610,031, 08/332,822, 07/988,589, 08/003, 778, 08/066,356, 08/438,705, 60/015,499, 60/003,149, 09/138,205, 09/138,209, 08/696,313, 60/012,316, 08/803, 469, 60/003,838, 08/709,998, 60/008,554, 08/762,478, 60/007,371, 08/850,424, 60/048,342, 09/080,751, 60/052, 907, 60/064,746, 09/111,995, 60/064,738, 60/065,376, 60/067,830, 60/089,498, 60/100,185, 09/081,164, 60/088, 283, 60/092,765, 07/244,988, 07/253,850; European Patents EP 0500686, EP 0610265, EP 0673370; PCT Application Numbers PCT/US90/06220, PCT/US94/08904, PCT/US94/ 10582, PCT/US95/02972, PCT/US95/10992, PCT/US93/ 04850, PCT/US95/12751, PCT/US96/00718, PCT/US93/ 03570, PCT/US93/09589, PCT/US96/05202, PCT/US97/ 03458, PCT/US96/12766, PCT/US97/01970, PCT/US96/ 14135, PCT/US96/19149, PCT/US96/17120, PCT/US98/ 09889, PCT/US98/13437;and U.S. Pat. Nos. 5,700,799, 5,719,154, 5,547,950, 5,523,403, 5,668,286, 5,652,238, 5,688,792, 5,247,090, 5,231,188, 5,654,428, 5,654,435, 5,756,732, 5,164,510, 5,182,403, 5,225,565, 5,618,949, 5,627,197, 5,534,636, 5,532,261, 5,776,937, 5,529,998, 5,684,023, 5,627,181, 5,698,574, 5,220,011, 5,208,329, 5,036,092, 4,965,268, 4,921,869, 4,948,801, 5,043,443, 5,130,316, 5,254,577, 4,877,892, 4,791,207, 4,642,351, 4,665,171, 4,734,495, 4,775,752, 4,870,169, 4,668,517, 4,340,606, 4,362,866, 4,193,918, 4,000,293, 3,947,465, 4,007,168, 3,674,780, 3,686,170, 3,906,101, 3,678,040, 3,177,114, 3,141,889, 3,149,119, 3,117,122, 5,719,154, 5,254,577, 4,801,600, 4,705,799, 4,461,773, 4,243,801, 3,794,665, 3,632,577, 3,598,830, 3,513,238, 3,598,812, 3,546,241, 3,318,878, 3,322,712; the disclosures of each of which are incorporated herein by reference in their entirety. Preferred oxazolidinones include linezolid and eperezolid.

The present invention is directed to novel photoaffinity probes comprising Formula I, Formula II, or Formula III. The preferred configuration at C-5 is (S). It will be appreciated by those skilled in the art that compounds of the present can have additional chiral centers and be isolated in optically active or racemic form. The present invention encompasses any racemic, optically-active (such as enantiomers, diastereomers), tautomeric, or stereoisomeric form, or mixture thereof, of a compound of the invention. The present invention is also directed to compositions comprising photoaffinity probes which comprise Formula I, Formula II, or Formula III, or a mixture thereof.

Preferred compounds of this invention have one radioactive element which is either $^3$H ($T_3$), $^{35}$S, or $^{125}$I. It is understood, however, that the Formulas include all isotopic forms of the compounds depicted.

In some embodiments of the invention, compounds comprise Formula I, shown below.

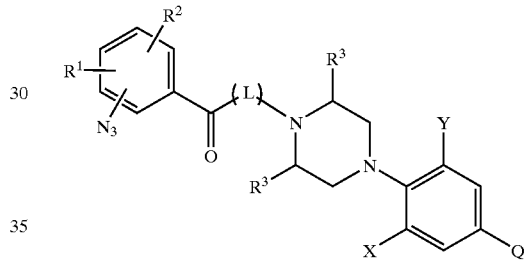

Formula I wherein X and Y are, independently, F, H or $CH_3$ in a variety of substitution patterns. Preferred compounds have one fluorine and one H. $R^1$ is H or I. $R^2$ is H or OH. $R^3$ is H or $C_1$–$C_8$ alkyl. L is a bond or —$OCH_2C(=O)$. Q is

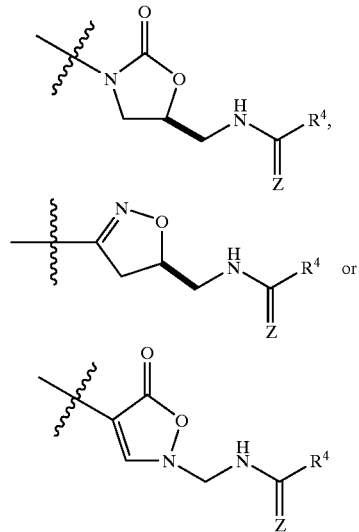

wherein $R^4$ is H, $CH_3$, $CH_2CH_3$ or cyclopropyl. Z is O or S. Compounds comprising Formula I also include pharmaceutically acceptable salts thereof.

Preferred compounds comprising Formula I have the following substituents: X is F, Y is H, $R^3$ is H, and $R^4$ is $CH_3$. More preferably, compounds of Formula I include, but are not limited to, 2-[4-[4-[(5S)-5-[(Acetylamino)methyl]-2-oxo-3-oxazolidinyl]-2-fluorophenyl ]-1-piperzinyl ]-2-oxoethyl-4-azido-2-hydroxy-5-iodo-$^{125}$I-benzoate, N-[[(5S)-3-[4-[4-(4-Azido-2-hydroxy-5-iodo-$^{125}$I-benzoyl)-1-piperazinyl]-3-fluorophenyl]-2-oxo-5-oxazolidinyl] methyl] acetamide, 2-[4-[4-[(5S)-5-[(Acetylamino)methyl]-2-oxo-3-oxazolidinyl]-2-fluorophen]-1-piperazinyl]-2-oxoethyl 4-azido-3-iodo-$^{125}$I-benzoate, and N-[[(5S)-3-[4-[4-(4-Azido-3-iodo-$^{125}$I-benzoyl)-1-piperazinyl]-3-fluorophenyl]-2-oxo-5-oxazolidinyl]methyl]acetamide.

In other embodiments of the invention, compounds comprise Formula II, shown below.

Formula II

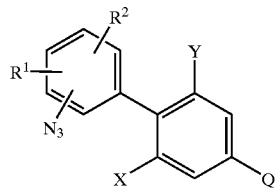

wherein X and Y are, independently, F, H or $CH_3$ in a variety of substitution patterns. Preferred compounds have one fluorine and one H. $R^1$ is H or I. $R^2$ is H or OH. Q is

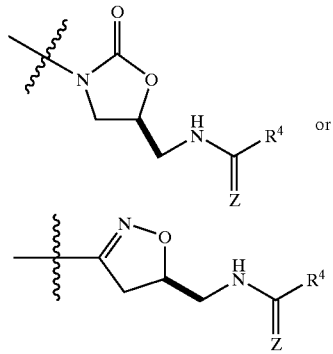

wherein $R^4$ is H, $CH_3$, $CH_2CH_3$ or cyclopropyl. Z is O or S. Compounds comprising Formula II also include pharmaceutically acceptable salts thereof.

Preferred compounds comprising Formula II have the following substituents: X is F, Y is H, and $R^4$ is $CH_3$. More preferably, compounds of Formula II include, but are not limited to, N-[[(5S)-3-(4'-Azido-2-fluoro[1,1'-biphenyl]-4-yl)-2-oxo-5-oxazolidinyl]methyl]-T$_3$-acetamide, N-[[(5S)-3-(4'-Azido-2-fluoro-3'-iodo[1,1'-biphenyl]-4-yl)-2-oxo-5-oxazolidinyl]methyl]-T$_3$-acetamide, N-[[(SS)-3-(4'-Azido-2-fluoro-3'-iodo[1,1'-biphenyl]-4-yl)-2-oxo-5-oxazolidinyl] methyl]ethane-$^{35}$S-thioamide, and N-[[(5S)-3-(4'-Azido-2-fluoro-3'-iodo-$^{125}$I-[1,1'-biphenyl]-4-yl)-2-oxo-5-oxazolidinyl]methyl]acetamide.

In other embodiments of the invention, compounds comprises Formula III, shown below.

Formula III

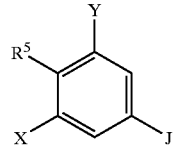

wherein X and Y are, independently, F, H or $CH_3$ in a variety of substitution patterns. Preferred compounds have one fluorine and one H. $R^5$ is

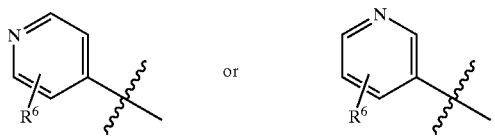

wherein $R^6$ is H, $N_3$, halogen, $NH_2$, OH, SH, $C_1$–$C_4$ alkylamino, $C_1$–$C_4$ dialkylamino, $C_1$–$C_4$ alkyl, nitrile, carboxamide, $C_1$–$C_4$ alkoxy, $C_1$–$C_4$ alkylthio, or $C_1$–$C_4$ alkoxycarbonyl. J is

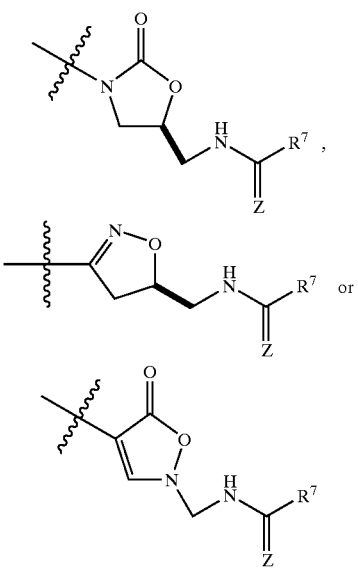

wherein Z is O or S. $R^7$ is

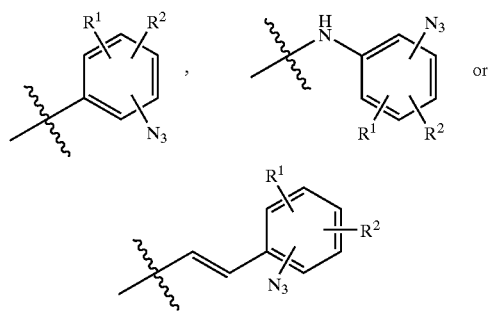

wherein $R^1$ is H or I, $R^2$ is H or OH. Compounds comprising Formula III also include pharmaceutically acceptable salts thereof.

Preferred compounds comprising Formula III have the following substituents: X is F, Y is H, and $R^6$ is H. More preferably, compounds of Formula III include, but are not limited to, (2E)-3-(4-azido-3-iodo-$^{125}$I-phenyl)-N-[[(5S)-3-[3-fluoro-4-(4-pyridinyl) phenyl]-2-oxo-5-oxazolidinyl] methyl]-2-propenamide, 4-azido-N-[[(5S)-3-[3-fluoro-4-(4-pyridinyl)phenyl]-2-oxo-5-oxazolidinyl]methyl]-2-hydroxy-5-iodo-$^{125}$I-benzamide, and N-(4-azidophenyl)-N'-[[(5S)-3-[3-fluoro-4-(4-pyridinyl)phenyl]-2-oxo-5-oxazolidinyl]methyl]-$^{35}$S-thiourea.

The present invention is also directed to methods of using a compound having Formula I, II, III, IV, V, or VI (shown above) as a photoaffinity probe. Briefly, a cell, or component (s) thereof, is contacted with a photoaffinity probe comprising Formula I, II, III, IV, V, or VI. Preferably, the photoaffinity probe is radiolabled. The photoaffinity probe is then exposed to light, preferably ultraviolet, in order to activate the photoaffinity probe. Cross-linking of the photoaffinity probe is determined by methods well known to those skilled in the art such as, for example, by detecting the radiolabel. Radiolabel, such as $^3$H, $^{125}$I, or $^{35}$S, for example, can be detected by a variety of autoradiography techniques well known to the skilled artisan. In other embodiments of the invention, the method further comprises contacting the cell or component(s) thereof with a competitor compound. The ability of the competitor compound to interfere with cross-linking of the photoaffinity probe indicates the bioactivity of the competitor compound.

Cells of the present invention include, but are not limited to, gram positive bacterial pathogens, including, for example, *Staphylococcus aureus; Staphylococcus epidermidis* (A, B, C biotypes); *Staphylococcus caseolyticus; Staphylococcus gallinarum; Staphylococcus haemolyticus; Staphylococcus hominis; Staphylococcus saprophyticus; Streptococcus agalactiae* (group B); *Streptococcus mutans/rattus; Streptococcus pneumoniae; Streptococcus pyogenes* (group A); *Streptococcus salivarius; Streptococcus sanguis; Streptococcus sobrinus; Actinomyces* spps.; *Arthrobacter histidinolovorans; Corynebacterium diptheriae; Clostridium difficle;* Clostridium spps.; *Enterococcus casseliflavus; Enterococcus durans; Enterococcus faecalis; Enterococcus faecium; Enterococcus gallinarum; Erysipelothrix rhusiopathiae;* Fusobacterium spps.; *Listeria monocytogenes; Prevotella* spps.; *Propionibacterium acnes*; and *Porphyromonas gingivalis*.

Cells also include, but are not limited to, gram negative bacterial pathogens, including, for example, *Acinetobacter calcoaceticus; Acinetobacter haemolyticus; Aeromonas hydrophila; Bordetella pertussis; Bordetella parapertussis; Bordetella bronchiseptica; Bacteroides fragilis; Bartonella bacilliformis; Brucella abortus; Brucella melitensis; Campylobacter fetus; Campylobacter jejuni; Chlamydia pneumoniae; Chlamydia psittaci; Chlamydia trachomatis; Citrobacter freundii; Coxiella burnetti; Edwardsiella tarda; Edwardsiella hoshinae; Enterobacter aerogenes, Enterobacter cloacae* (groups A and B); *Escherichia coli* (to include all pathogenic subtypes) *Ehrlicia* spps.; *Francisella tularensis; Haemophilus actinomycetemcomitans; Haemophilus ducreyi; Haemophilus haemolyticus; Haemophilus influenzae; Haemophilus parahaemolyticus; Haemophilus parainfluenzae; Hafnia alvei; Helicobacter pylori; Kingella kingae; Klebsiella oxytoca; Klebsiella pneumoniae; Legionella pneumophila; Legionella* spps.; *Morganella* spps.; *Moraxella cattarhalis; Neisseria gonorrhoeae; Neisseria meningitidis; Plesiomonas shigelloides; Proteus mirabilis; Proteus penneri;* Providencia spps.; *Pseudomonas aeruginosa; Pseudomonas species; Rickettsia prowazekii; Rickettsia rickettsii; Rickettsia tsutsugamushi;* Rochalimaea spps.; *Salmonella* subgroup 1 serotypes (to include *S. paratyphi* and *S. typhi*); *Salmonella* subgroups 2, 3a, 3b, 4, and 5; *Serratia marcesans; Serratia* spps.; *Shigella boydii; Shigella flexneri; Shigella dysenteriae; Shigella sonnei; Yersinia enterocolitica; Yersinia pestis; Yersinia pseudotuberculosis; Vibrio cholerae; Vibrio vulnificus*; and *Vibrio parahaemolyticus*.

Cells also include, but are not limited to, Mycobacterial species, including, for example, *Mycobacterium tuberculosis; Mycobacterium avium*; and other *Mycobacterium* spps.

Cells also include, but are not limited to, Mycoplasmas (or pleuropneumonia-like organisms), including, for example, *Mycoplasma genitalium; Mycoplasma pneumoniae*; and other *Mycoplasma* spps.

Cells also include, but are not limited to, Treponemataceae (spiral organisms) including, for example, *Borrelia burgdorferi*; other *Borrelia* species; Leptospira spps.; *Treponema pallidum*.

Methods for preparing the photoaffinity probes described in Formulas I, II, III, IV, V, and VI are depicted in the following synthesis schemes. It will be apparent to those skilled in the art that the described synthetic procedures are merely representative in nature and that alternative procedures are feasible and may be preferred in some cases.

Non-radioactive compounds of Formulas I and IV are prepared by the methods described in Schemes A and B. As shown in Scheme A, coupling of a benzoic acid moiety ($A_1$) with an appropriate hydroxyacetyl piperazine fragment ($A_2$) leads to compounds $A_3$ of Formula I where L is —OCH$_2$C (=O). Coupling can be accomplished with 1-[3-(dimethylamino)propyl]-3-ethylcarbodiimide hydrochloride or any other reagents familiar to ones skilled in the art. Appropriate benzoic acid fragments can be made by procedures known in the literature. (Dupuis, *Can. J. Chem.*, 1987, 65, 2450–2453; Shu, *J. Labelled Compounds and Radiopharmaceuticals*, 1996, 38, 227–237, each of which is incorporated herein by reference in its entirety). Appropriate hydroxyacetyl piperazine fragments can also be made by methods known in the literature (Barbachyn, U.S. Pat. No. 5,547,950; Barbachyn, U.S. Pat. No. 5,990,136; and Synder, International Publication WO 00/10566-A1, each of which is incorporated herein by reference in its entirety). Methods for incorporation of $^{125}$I into compounds $A_3$ are shown in Schemes C and D.

Scheme A:

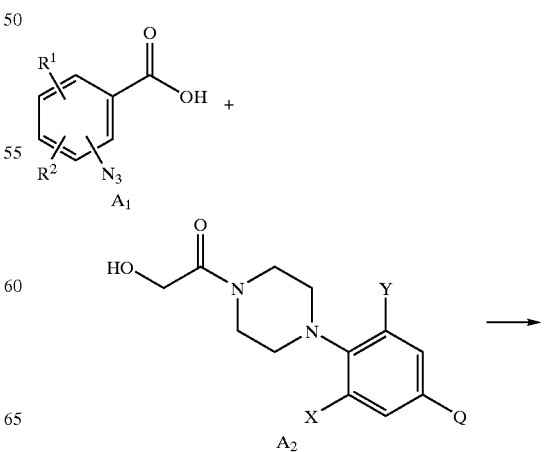

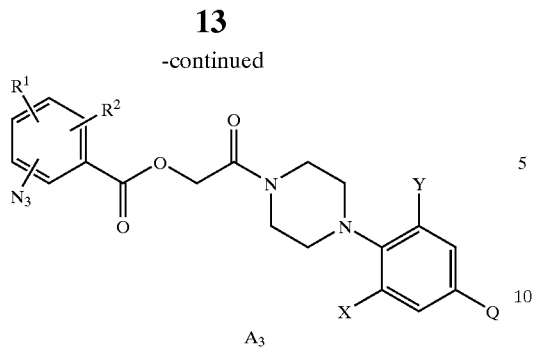

A₃

Non-radioactive compounds of Formulas I and IV where L is a bond are prepared by the synthetic sequence shown in Scheme B. An appropriate benzoic acid fragment (A₁ of Scheme A) is coupled with an appropriate piperazine (B₂) using 1,1-carbonyldiimidazole in tetrahydrofuran to give the desired compound (B₃) Other coupling methods known to those skilled in the art are also possible. The piperazine fragment is made by methods known in the literature (Hutchinson, U.S. Pat. No. 5,700,799, which is incorporated herein by reference in its entirety; Barbachyn, U.S. Pat. No. 5,990,136; and Snyder, International Publication WO 00/10566-A1). Methods for incorporation of $^{125}I$ into compounds B₃ are shown in Schemes C and D.

Scheme B:

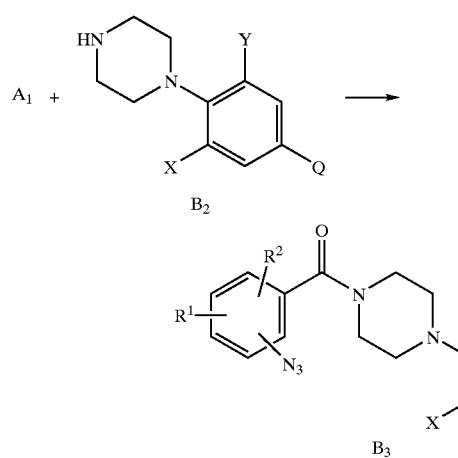

Radioactive iodine is introduced into the compounds of Formulas I and IV by the methods shown in Schemes C and D. Compounds C₂ of Formula I (where R¹ is OH and R² is $^{125}I$) are prepared by reaction of compounds C₁ (prepared according to the methods of Schemes A and B) with Na$^{125}$I and chloramine-T.

Scheme C:

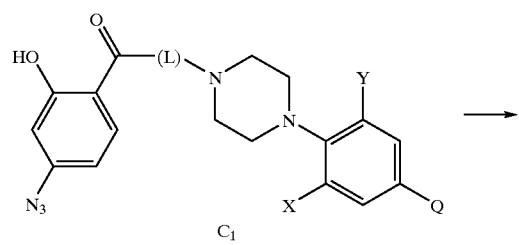

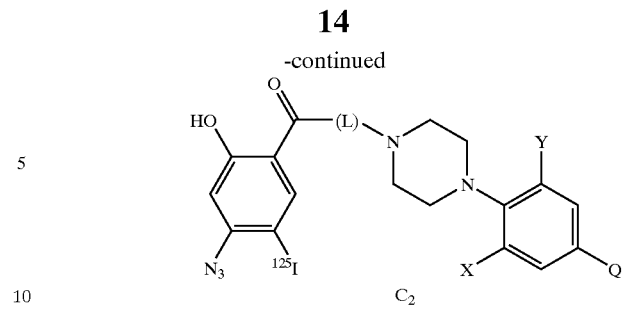

C₂

Alternatively, compounds D₃ of Formulas I and IV (where R¹ is H and R² is $^{125}I$) are prepared as shown in Scheme D. Reaction of compounds D₁ (prepared by the methods shown in Schemes A and B) with hexamethylditin affords the stannanes D₂. Reaction of D₂ with Na$^{125}$I and chloramine-T leads to D₃.

Scheme D:

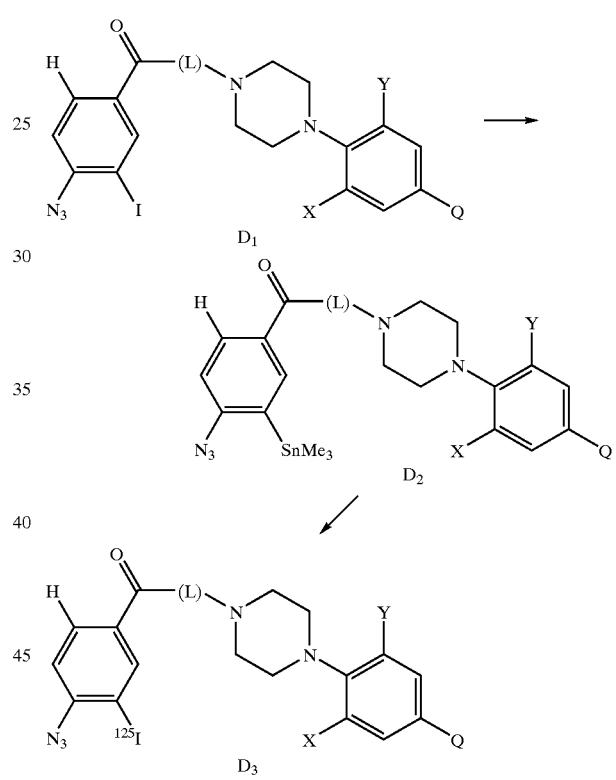

Non-radioactive compounds of Formulas II and V are prepared by the method shown in Scheme E. The appropriate biphenyl nitro fragment (E₁) is reduced in the presence of hydrogen gas and a palladium catalyst to give the appropriate biphenyl aniline fragment (E₂). Other reduction methods familiar to those skilled in the art may also be used. Conversion to the azido moiety (E₃) can be accomplished via displacement of the appropriate diazonium salt with sodium azide using conditions familiar to those skilled in the art. The appropriate nitro fragments (E₁) can be prepared by methods known in the literature (Barbachyn, U.S. Pat. No. 5,654,435, which is incorporated herein by reference in its entirety; Barbachyn U.S. Pat. No. 5,990,136; and Synder, International Publication WO 00/10566-A1) or by other methods familiar to those skilled in the art. Introduction of radioactive elements into compounds of Formulas II and V are depicted in Schemes F, G, and H.

Scheme E:

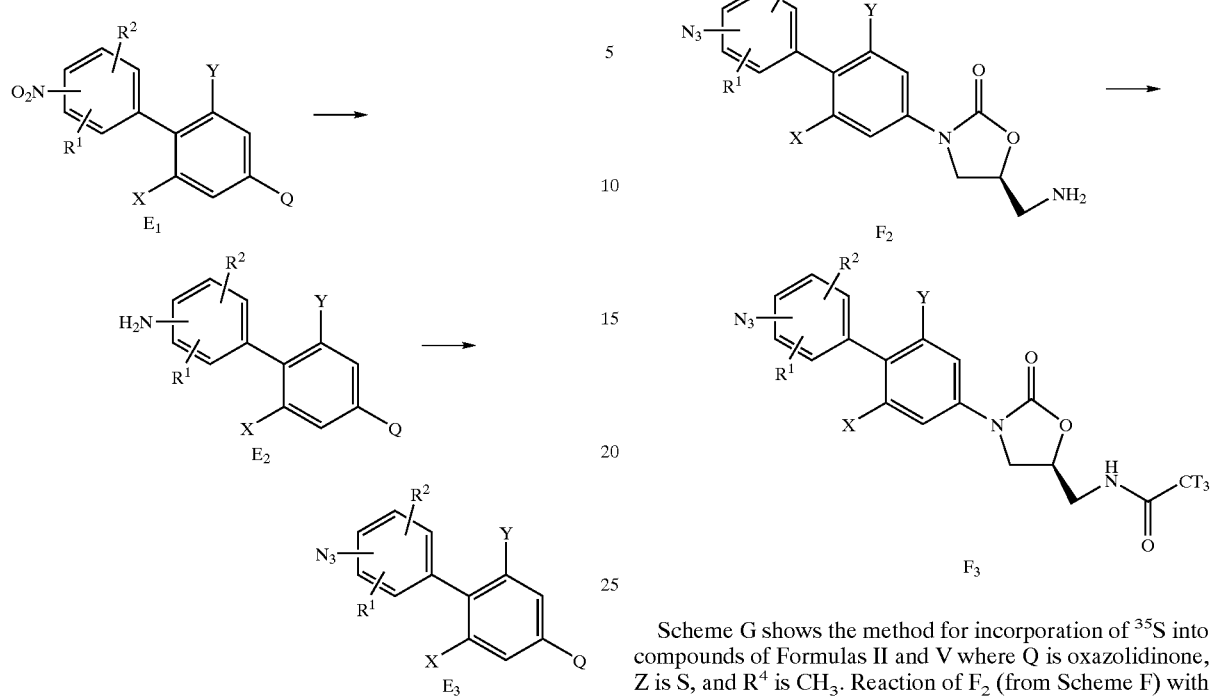

Scheme F shows the procedure for incorporation of tritium into compounds of Formulas II and V where Q is oxazolidinone, Z is O, and $R^4$ is $CH_3$. Reaction of $F_1$ (prepared according to Scheme E) with 6N HCl and methanol affords the free amine $F_2$. Reaction of $F_2$ with tritiated sodium acetate and a coupling reagent affords the tritiated acetainide $F_3$. Suitable coupling reagents include O-benzotriazol-1-yl-N,N,N',N',tetramethyluronium hexafluorophosphate and O-(7-azabenzotriazol-1-yl)-N,N,N',N'-tetramethyluronium hexafluorophosphate. Other acceptable coupling reagents are known by those skilled in the art. Alternatively, tritiated acetic anhydride and a suitable base can be used in place of tritiated sodium acetate and a coupling reagent. Incorporation of tritium into compounds of Formulas II and V where Q is isoxazoline is carried out in similar fashion.

Scheme F:

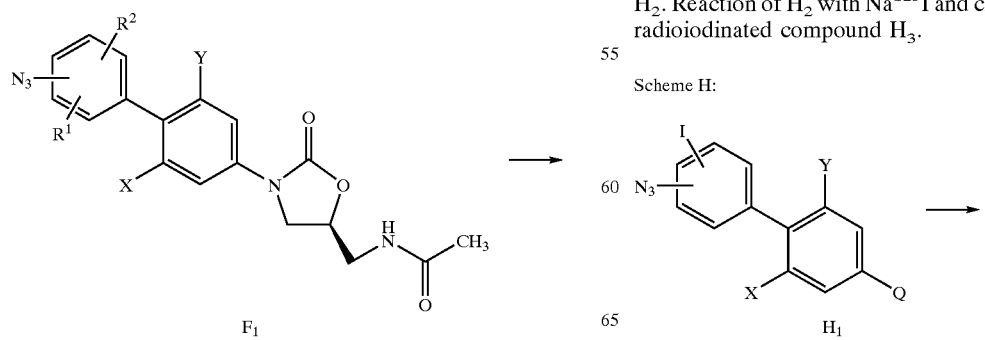

Scheme G shows the method for incorporation of $^{35}S$ into compounds of Formulas II and V where Q is oxazolidinone, Z is S, and $R^4$ is $CH_3$. Reaction of $F_2$ (from Scheme F) with ethyl $^{35}S$-dithioacetate affords the $^{35}S$-thioacetamide, $G_2$. Incorporation of $^{35}S$ into compounds of Formulas II and V where Q is isoxazoline is carried out in similar fashion.

Scheme G:

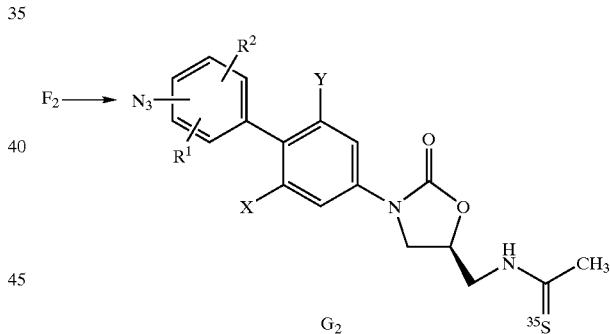

Radioactive iodine can be introduced into compounds of Formulas II and V by the method shown in Scheme H. Reaction of $H_1$ (prepared according to the route shown in Scheme E) with hexamethylditin affords the organostannane $H_2$. Reaction of $H_2$ with $Na^{125}I$ and chloramine-T affords the radioiodinated compound $H_3$.

Scheme H:

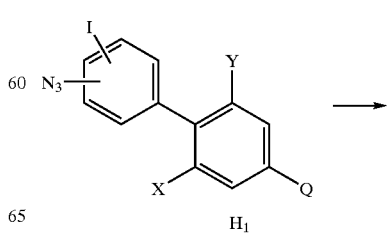

-continued

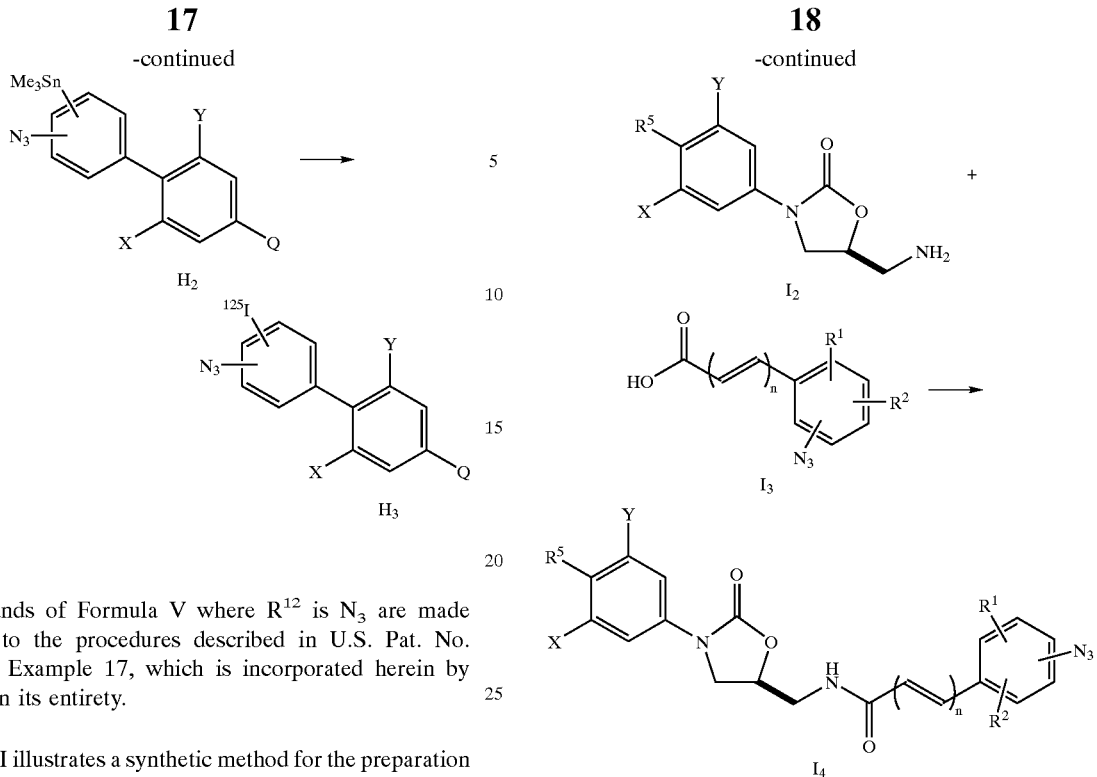

Compounds of Formula V where $R^{12}$ is $N_3$ are made according to the procedures described in U.S. Pat. No. 5,910,504, Example 17, which is incorporated herein by reference in its entirety.

Scheme I illustrates a synthetic method for the preparation of non-radioactive compounds of Formulas III and VI where J is oxazolidinone, Z is O, and $R^7$ is optionally substituted azidophenyl or azidocinnamoyl. Refluxing an appropriate acetamide fragment ($I_1$) in methanolic hydrochloric acid affords the free amine $I_2$. The acetamide fragments ($I_1$) are prepared by methods known in the literature (Barbachyn, U.S. Pat. No. 5,565,571, which is incorporated herein by reference in its entirety; Barbachyn, U.S. Pat. No. 5,990, 136; and Synder, International Publication WO 00/10566-A1). Coupling of $I_2$ with an appropriate benzoic acid fragment ($I_3$, n=0) or cinnamic acid fragment ($I_3$, n=1) leads to the amide $I_4$. Coupling can be accomplished with EDC or other reagents familiar to ones skilled in the art. Appropriate benzoic acid fragments ($I_3$, n=0) are prepared by the same method used to prepare $A_1$ of Scheme A. Appropriate cinnamic acid fragments ($I_3$, n=1) can be prepared by coupling of an appropriate benzaldehyde with Wittig-Horner reagents. Benzaldehyde fragments can be prepared by procedures known in the literature (Shu, *J. Labelled Compounds and Radiopharmaceuticals*, 1996, 38, 227–237) or by other methods familiar to those skilled in the art. Compounds of Formulas III and VI where J is isoxazoline or isoxazolinone are made by similar methods.

Scheme I:

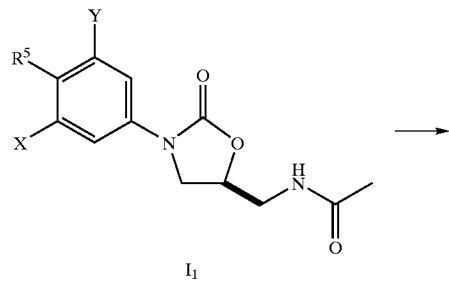

Introduction of $^{125}I$ into compounds of Formulas III and VI where J is oxazolidinone, Z is O, and $R^7$ is optionally substituted azidophenyl or azidocinnamoyl is accomplished by the method shown in Scheme J. Reaction of $I_4$ (from Scheme I, where $R^1$ is H and $R^2$ is OH) with $Na^{125}I$ and chloramine-T affords the radioiodinated compound $J_2$. Introduction of $^{125}I$ into compounds of Formulas III and VI where J is isoxazoline or isoxazolinone is carried out by similar methods.

Scheme J:

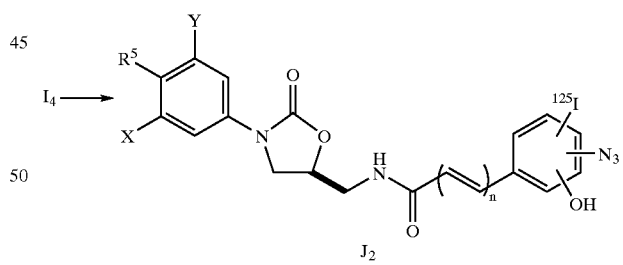

Alternatively, introduction of $^{125}I$ into compounds of Formulas III and VI where J is oxazolidinone, Z is O, and $R^7$ is optionally substituted azidophenyl or azidocinnamoyl is carried out by the method shown in Scheme K. Reaction of $I_4$ (from Scheme I, where $R^1$ is I and $R^2$ is H) with hexamethylditin affords the organostannane $K_2$. Reaction of $K_2$ with $Na^{125}I$ and chloramine-T affords the radioiodinated compound $K_3$. Radioiodination of compounds of Formulas III and VI where J is isoxazoline or isoxazolinone is carried out in similar fashion.

Scheme K:

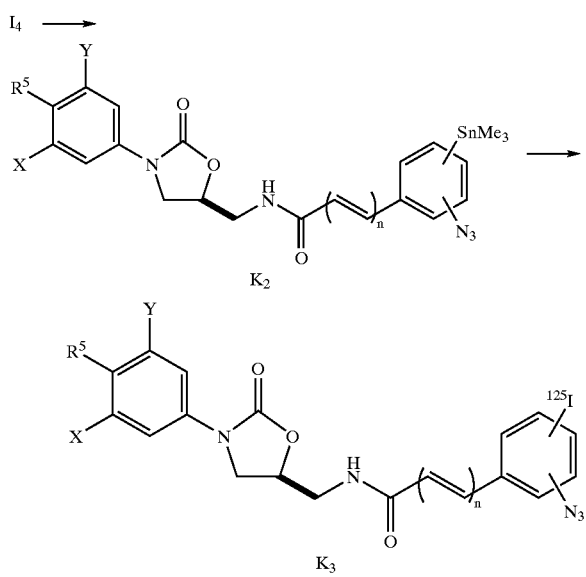

Scheme L illustrates a synthetic method for the preparation of radioactive compounds of Formulas III and VI where J is oxazolidinone, Z is $^{35}S$, and $R^7$ is optionally substituted azidoaniline. An appropriate $^{35}S$-isothiocyanate $L_2$ is reacted with the appropriate aminomethyl fragment $I_2$ (Scheme I) in refluxing THF to give the desired $^{35}S$-thiourea, ($L_3$). The required $^{35}S$-isothiocyanate $L_2$ is prepared by reaction of an appropriate aniline with $^{35}S$-thiophosgene. Introduction of $^{35}S$ into compounds of Formulas III and VI where J is isoxazoline or isoxazolinone is carried out in similar fashion.

Scheme L:

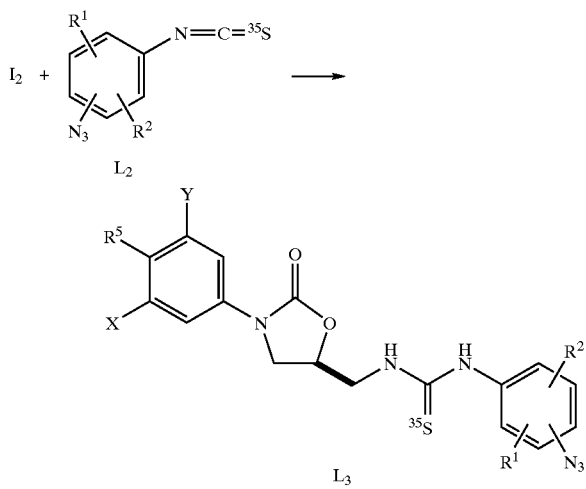

The invention is further illustrated by way of the following examples which are intended to elucidate the invention. These examples are not intended, nor are they to be construed, as limiting the scope of the disclosure.

EXAMPLES

Example 1

Synthesis

2-[4-[4-[(S)-5-[(Acetylamino)methyl]-2-oxo-3-oxazolidinyl]-2-fluorophenyl]-1-piperazinyl]-2-oxoethyl 4-azido-2-hydroxy-5-iodo-$^{125}$I-benzoate (Compound $C_2$ of Scheme C where L is —$CH_2C(=O)$, X is F, Y is H, Q is oxazolidinone, Z is O and $R^4$ is $CH_3$) is prepared as follows.

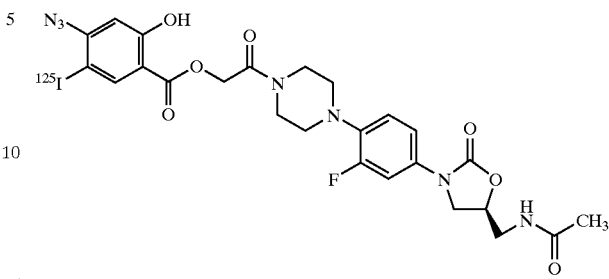

Step 1. To a stirred solution of (S)-N-[[3-[3-fluoro-4[4-(hydroxyacetyl)-1-piperazinyl]phenyl]-2-oxo-5-oxazolidinyl]methyl]acetamide (515.8 mg, 1.31 mmol) in dimethylformamide (10 ml) and pyridine (1 ml) is added 1-[3-(dimethylamino)propyl]-3-ethylcarbodiimide hydrochloride (509.9 mg, 2.66 mmol) followed by 4-azidosalicylic acid (Dupuis, Can. J Chem., 1987, 65, 2450–2453) and a catalytic amount of 4-dimethylaminopyridine. The reaction mixture is stirred at room temperature for 72 hours then concentrated. The residue is diluted with $CH_2Cl_2$ (100 ml) and is washed successively with $H_2O$ (2×30 ml), 1 N HCl (2×30 ml), saturated $NaHCO_3$ (1×30 ml), dried ($MgSO_4$), filtered and concentrated. The residue is dissolved in $CH_3OH/CH_2Cl_2$, absorbed onto silica gel and is purified on a Biotage 40S column with a SIM using 2.5% $CH_3OH$ in $CH_2Cl_2$ as the eluent to give 186.5 mg (0.33 mmol, 25%) of the benzoate ester. mp 177–178° C. (dec). $^1$H-NMR (DMSO) δ: 10.4, 8.24, 7.87, 7.53, 7.17, 7.09, 6.76, 6.70, 5.17, 4.71, 4.09, 3.71, 3.60, 3.40, 3.02, 2.96, 1.83.

Step 2. All reagents are prepared in 0.1 N $NaPO_4$ buffer, pH 7.4 unless otherwise specified. Buffer (70 µl), chloramine-T (70 µl of a 1 mM stock solution), and the azido phenol of Step 1 (10 µl of a 50 µM stock solution in DMSO) are added to a 1.5 ml glass reaction vial. A rubber septum cap is crimped onto the reaction vial and a solution of $^{125}I_2$ in sodium hydroxide (10 µl containing 1 mCi (Amersham #IMS 30) is added. The reaction is gently vortexed in the dark for 2 hours at room temperature then quenched with 10% solution of sodium bisulfite (100 µl). The quenched reaction is diluted with buffer (800 µl) and transferred from the reaction vial with a 1 ml tuberculin syringe fitted with an 18 gauge needle. The reaction volume (1 ml) is loaded onto a preconditioned C18 sep-pak cartridge (Millipore Corporation) and the unincorporated $^{125}I_2$ is washed from the C18 resin with HPLC grade water containing 0.1% trifluoroacetic acid (20 ml). Product is eluted using of 80% $CH_3CN/0.1$ TFA (3 ml). The typical yield of iodinated product is approximately 30% of the total $^{125}I_2$ added to the reaction.

Example 2

Synthesis

N-[[(5S)-3-[4-[4-(4-Azido-2-hydroxy-5-iodo-$^{125}$I-benzoyl)-1-piperazinyl]-3-fluorophenyl]-2-oxo-5-oxazolidinyl]methyl]acetamide (Compound $C_2$ of Scheme C where L is a bond, X is F, Y is H, Q is oxazolidinone, Z is O and $R^4$ is $CH_3$) is prepared as follows.

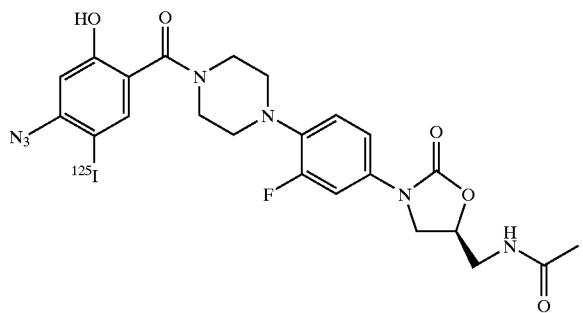

Step 1. To a stirred suspension of (S)-N-[[3-[4-[3-fluoro-4-(1-piperazinyl)]phenyl]-2-oxo-5-oxazolidinyl]methyl]-acetamide (498.0 mg, 1.3 mmol) in CH$_2$Cl$_2$ (10 ml) is added diisopropylethylamine (0.70 ml, 4.0 mmol) followed by 4-azidosalicoyl chloride (342.6 mg, 1.7 mmol) in CH$_2$Cl$_2$ (7 ml). The reaction mixture is stirred at room temperature for 18 hours and then is partitioned between CH$_2$Cl$_2$ (50 ml) and H$_2$O (10 ml). The phases are separated. The organic layer is washed with H$_2$O (10 ml), dried (MgSO$_4$), filtered and concentrated. The residue is dissolved in CH$_3$OH/CH$_2$Cl$_2$, absorbed onto silica gel and is purified on a Biotage 40S column with a SIM using 3% CH$_3$OH in CH$_2$Cl$_2$ as the eluent to afford 412.3 mg (0.83 mmol, 62%) of the desired benzamide as a tan solid. mp 188–189° C. (dec). $^1$H-NMR (DMSO) δ: 10.2, 8.24, 7.51, 7.22, 7.16, 7.07, 6.64, 6.58, 4.70, 4.07, 3.70, 3.36, 2.96, 1.83.

Step 2. Starting with the phenol prepared in Step 1, $^{125}$I is introduced according to the procedure described in Step 2 of example 1.

Example 3

Synthesis

2-[4-[4-[(5S)-5-[(Acetylamino)methyl]-2-oxo-3-oxazolidinyl]-2-fluorophenyl]-1-piperazinyl]-2-oxoethyl 4-azido-3-iodo-$^{125}$I-benzoate (Compound D$_3$ of Scheme D where L is —CH$_2$C(=O), X is F, Y is H, Q is oxazolidinone, Z is O and R$^4$ is CH$_3$)

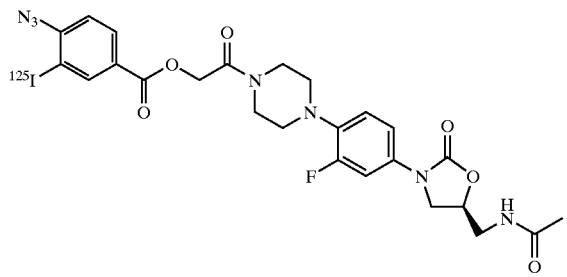

Step 1. To a stirred solution of 4-azido-3-iodobenzoic acid (103.8 mg, 0.36 mmol, (Shu, *J. of Labelled Compounds and Radiopharmaceuticals*, 1996, 38, 227–237)) in dry THF (2.0 ml) is added 1,1-carbonyldiimidazole (58.2 mg, 0.36 mmol). The reaction mixture is stirred at room temperature for 1 hour, then (S)-N-[[3-[3-fluoro-4[4-(hydroxyacetyl)-1-piperazinyl]phenyl]-2-oxo-5-oxazolidinyl]methyl]-acetamide (141.9 mg, 0.36 mmol) is added followed by a catalytic amount of DMAP. The reaction mixture is heated at reflux for 72 hours. The reaction mixture was cooled to room temperature and poured into CH$_2$Cl$_2$ (30 ml) and washed successively with H$_2$O (15 ml), 1 N HCl (15 ml), saturated aqueous NaHCO$_3$ (15 ml), brine (15 ml), dried (MgSO$_4$), filtered and concentrated. The residue is purified on a Biotage 12M column using 2% CH$_3$OH in CH$_2$Cl$_2$ as the eluent to afford 119.6 mg (0.18 mmol, 50%) of the benzoate ester. mp 137–139 ° C. $^1$H-NMR (CDCl$_3$) δ: 8.52, 8.14, 7.49, 7.19, 7.07, 6.95, 6.01, 5.00, 4.72, 4.02, 3.81, 3.75, 3.62, 3.05, 1.58.

Step 2. To a stirred solution of the iodobenzoate prepared in Step 1 (62.7 mg, 0.094 mmol) and hexamethylditin (46.3 mg, 0.14 mmol) in dry THF (3 ml) is added dichlorobis(triphenylphosphine)palladium (II) (2.0 mg, 0.003 mmol). The reaction mixture is degassed and is heated at reflux for 3 hours. The reaction mixture is cooled and filtered through a pad of celite. The filtrate is absorbed onto silica gel and purified on a Biotage 12M column with SIM using 2% CH$_3$OH in CH$_2$Cl$_2$ as the eluent to afford 28.6 mg (0.04 mmol, 43%) of the stannane. $^1$H-NMR (DMSO) δ: 8.25, 8.04, 8.00, 7.48, 7.42, 7.15, 7.10, 5.10, 4.73, 4.09, 3.71, 3.60, 3.40, 3.02, 2.96, 1.83, 0.33.

Step 3. To a stirred solution of the stannane prepared in Step 2 in dry acetonitrile is added a solution of 1M aqueous Na$^{125}$I followed by chloramine-T hydrate. After stirring at room temperature for 30 minutes, the reaction mixture is quenched with saturated aqueous Na$_2$S$_2$O$_3$ and purified to give the radioiodinated material.

Example 4

Synthesis

N-[[(5S)-3-[4-[4-(4-Azido-3-iodo-$^{125}$I-benzoyl)-1-piperazinyl]-3-fluorophenyl]-2-oxo-5-oxazolidinyl]methyl]acetamide (Compound D$_3$ of Scheme D where L is a bond, X is F, Y is H, Q is oxazolidinone, Z is O and R$^4$ is CH$_3$)

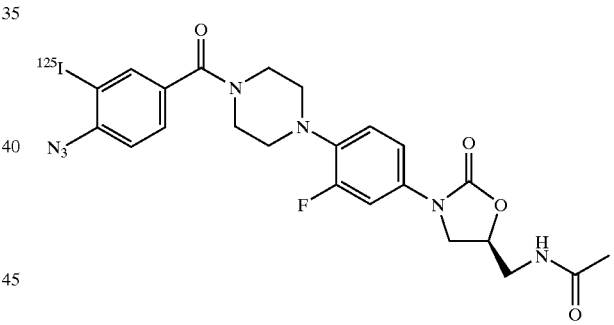

Step 1. To a stirred solution of 4-azido-3-iodobenzoic acid (272.0 mg, 0.94 mmol) in dry THF (4 ml) is added 1,1-carbonyldiimidazole (152.6 mg, 0.94 mmol). The reaction mixture is stirred at room temperature for 1 hour, then (S)-N-[[3-[4-[3-fluoro-4-(1-piperazinyl)]phenyl]-2-oxo-5-oxazolidinyl]methyl]-acetamide (315.9 mg, 0.94 mmol) is added followed by DMF (2 ml). The reaction mixture is heated at reflux for 18 hours. The reaction mixture is cooled and poured into CH$_2$Cl$_2$ (40 ml) and successively washed with H$_2$O (20 ml), 1 N HCl (20 ml), saturated aqueous NaHCO$_3$ (20 ml), brine (20 ml), dried (MgSO$_4$), filtered and concentrated. The residue is dissolved in CH$_2$Cl$_2$, absorbed onto silica gel and is purified on a Biotage 40S column with SIM using 2.5% CH$_3$OH in CH$_2$Cl$_2$ as the eluent to afford 376.7 mg (0.62 mmol) of the benzamide as a yellow solid. $^1$H-NMR (DMSO) δ: 8.24, 7.88, 7.53, 7.47, 7.39, 7.19, 7.08, 4.71, 4.08, 3.70, 3.51, 3.40, 2.99, 1.83.

Step 2. To a stirred solution of the iodobenzamide prepared in Step 1 (82.4 mg, 0.13 mmol) and hexamethylditin (71.1 mg 0.22 mmol) in dry THF (6 ml) is added tetrakis(triphenylphosphine)palladium(0). The reaction mixture is degassed and heated at reflux for 12 hours. The cooled reaction mixture is filtered through a plug of celite and the filtrate is absorbed onto silica gel and purified on a Biotage 12M column with SIM using 2% $CH_3OH$ in 49% $CH_2Cl_2$ and 49% EtOAC as the eluent to afford 28.2 mg (0.044 mmol, 34%) of the stannane. $^1$H-NMR (DMSO) δ: 8.24, 7.50, 7.43, 7.35, 7.18, 7.17, 4.71, 4.08, 4.01, 3.70, 3.40, 2.99, 1.83, 0.32.

Step 3. To a stirred solution of the stannane prepared in Step 2 in dry acetonitrile is added a solution of 1M aqueous $Na^{125}I$ followed by chloramine-T hydrate. After stirring at room temperature for 30 minutes, the reaction mixture is quenched with saturated aqueous $Na_2S_2O_3$ and purified to give the desired radioiodinated material.

Example 5

Synthesis

N-[[(5S)-3-(4'-Azido-2-fluoro[1,1'-biphenyl]-4-yl)-2-oxo-5-oxazolidinyl]methyl]-$T_3$-acetamide (Compound $F_3$ of Scheme F where $R^1$ is H, $R^2$ is H, X is F, and Y is H)

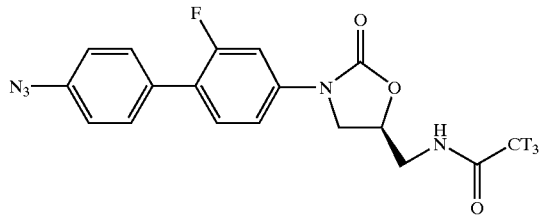

Step 1. To a stirred solution of 4-iodonitrobenzene (6.86 g, 27.5 mmol) in dry DMF (230 ml) is added bis(pinacolato)diboron (8.24 g, 32.4 mmol) followed by potassium acetate (8.68 g, 88.5 mmol) and [1,1'-bis(diphenylphosphino)ferrocene]dichloropalladium(II) (624.6 mg, 0.76 mmol). The reaction mixture is degassed and heated at 85° C. for 2 hours. To the cooled dark reaction mixture is added (S)-N-[[3-(3-fluoro-4-iodophenyl)-2-oxo-5-oxazolidinyl]methyl]acetamide (5.8 g, 15.3 mmol) followed by 2 N aqueous $NaC_2O_3$ (143 ml) and [1,1'-bis (diphenylphosphino)ferrocene]dichloropalladium(II) (312.0 mg, 0.38 mmol). The reaction mixture is degassed and heated at 85° C. for 3 hours. The cooled reaction mixture is partitioned between EtOAC (500 ml) and $H_2O$ (300 ml). The phases are separated. The aqueous layer is extracted with EtOAC (300 ml). The organic layers are combined and successively washed with $H_2O$ (500 ml), brine (500 ml), dried ($MgSO_4$), filtered and concentrated. The residue is dissolved in $CH_3OH/CH_2Cl_2$, absorbed onto silica gel and is purified on a Biotage 40 M column (2 lots) with SIM using 75% EtOAC in $CH_2Cl_2$ to 100% EtOAC as the eluent to afford 3.74 g (10.0 mmol, 65%) of the desired nitrobiphenyl compound. $^1$H-NMR (DMSO) δ: 8.30, 7.83, 7.68, 7.50, 4.78, 4.18, 3.80, 3.44, 1.84.

Step 2. A mixture of the nitrobiphenyl compound prepared in Step 1 (3.74 g, 10.0 mmol), 10% palladium on carbon in THF (100 ml), $CH_3OH$ (100 ml) and $CH_2Cl_2$ (100 ml) is hydrogenated under a balloon of hydrogen for 18 hours. The reaction mixture is filtered through a pad of celite and the filtrate is concentrated to afford 2.50 g (7.3 mmol, 73%) of the desired aminobiphenyl. $^1$H-NMR (DMSO) δ: 8.26, 7.45, 7.34, 7.23, 6.64, 5.28, 4.73, 4.14, 3.76, 3.42, 1.84.

Step 3. To a stirred solution of the aminobiphenyl prepared in Step 2 (508.93 mg, 1.48 mmol) in $CH_3OH$ (40 ml) and 1 M HCl (40 ml), cooled to 0° C. is added a 1.2 M aqueous $NaNO_2$ solution (1.48 ml, 1.78 mmol). The reaction mixture is stirred at 0° C. for 90 minutes, then sulfamic acid (143.5 mg, 1.48 mmol) is added followed by sodium azide (115.4 mg, 1.78 mmol) in $H_2O$ (1.5 ml). The reaction mixture is stirred at 0° C. for 45 minutes, then diluted with $CH_2Cl_2$ (200 ml). The phases are separated. The aqueous phase is extracted with $CH_2Cl_2$ (75 ml). The combine organic phases are dried ($MgSO_4$), filtered and concentrated. The residue is dissolved in $CH_3OH/CH_2Cl_2$, absorbed onto silica gel and is purified on a Biotage 40S column with SIM using 10% $CH_3OH$ in $CH_2Cl_2$ as the eluent to afford 262.9 mg (0.71 mmol, 48%) of the desired azidobiphenyl as a pale yellow solid. $^1$H-NMR (DMSO) δ: 8.27, 7.58, 7.42, 7.24, 4.76, 4.16, 3.78, 3.43, 1.84.

Step 4. The azidobiphenyl prepared in Step 3 (102.4 mg, 0.27 mmol) in 6 N HCl (2 ml) and $CH_3OH$ (6 ml) is heated at reflux for 18 hours. The $CH_3OH$ is removed in vacuo and the solid precipitate is isolated by filtration and is washed successively with $H_2O$ (10 ml), ether (2×15 ml) then dried to afford 82.1 mg (0.23 mmol, 82%) of the desired amine hydrochloride. $^1$H-NMR (DMSO) δ: 8.30, 7.62, 7.42, 7.25, 4.98, 4.25, 3.91.

Step 5. To a stirring solution of 0.57 mg (6.94 μmol, 250 mCi) of tritiated acetic acid sodium salt (American Radiolabeled Chemicals, lot no ARC 990519) in 1 ml of dry DMF and 2.71 mg (21 μmol) of diisopropylethylamine at room temperature, is added 6.94 μmol of 0.45M O-Benzotriazol-1-yl-N,N,N',N'-tetramethyluronium hexafluorophosphate (HBTU) in dry DMF. The solution instantly turned pale yellow and is stirred at room temperature for 10 minutes. The activated [$^3$H]acetic acid sodium salt was then added to a stirring solution of 2.73 mg (7.5 μmol) of the amine hydrochloride prepared in Step 4 in 2 ml of dry DMF. The reaction is stirred at room temperature for 4.5 hours, then all solvents are removed by vacuum distillation at room temperature. The crude reaction mixture is purified on a preparative TLC plate (Analtech Silica gel GF, 500 micron, 20 cm×20 cm plate), eluted with 8% methanol in dichloromethane. The desired band is scrapped. The product is eluted from the silica gel with 20% methanol in dichloromethane and filtered. The filtrate is concentrated under vacuum, and the residue is dissolved in 65.5 ml of methanol to afford 94.4 mCi of the desired tritiated material (1.44 mCi/ml methanol, specific activity 57.37 mCi/mg (57.37 Ci/mmol), radiochemical purity 99.5% by HPLC).

Example 6

Synthesis

N-[[(5S)-3-(4'-Azido-2-fluoro-3'-iodo[1,1'-biphenyl]-4-yl)-2-oxo-5-oxazolidinyl]methyl]-$T_3$-acetamide (Compound $F_3$ of Scheme F where $R^1$ is H, $R^2$ is I, X is F, and Y is H)

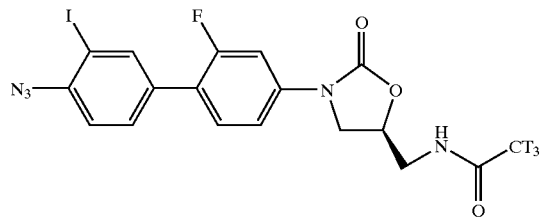

Step 1. To a stirred solution of the aniline prepared in Step 2 of Example 5 (284.9 mg, 0.83 mmol) in acetic acid (3 ml)

is added iodine monochloride (134.5 mg, 0.83 mmol) in acetic acid (0.25 ml). The reaction mixture is stirred at room temperature for 1.5 hours. The reaction mixture is partitioned between EtOAc and aqueous $Na_2S_2O_3$. The phases are separated. The aqueous phase is extracted with EtOAc (20 ml). The combined organic phases were dried ($MgSO_4$), filtered and concentrated. The residue is dissolved in $CH_3OH$, absorbed onto silica gel and is purified on a Biotage 40S column with SIM using 10–25% acetone in $CH_2Cl_2$ as the eluent to afford 48.4 mg (0.10 mmol, 12%) of the desired iodoaniline as a yellow oil. $^1$H-NMR ($CH_3OD$) δ: 7.73, 7.52, 7.29, 6.85, 4.81, 4.10, 3.79, 3.53, 3.32, 1.98.

Step 2. To a stirred solution of the iodoaniline prepared in Step 1 (47.2 mg, 0.10 mmol) in $CH_3OH$ (2 ml) and 1N HCl (2 ml) cooled to 0° C., is added a solution of $NaNO_2$ (8.5 mg, 0.12 mmol) in $H_2O$ (1 ml). The yellow reaction mixture is stirred at 0° C. for 30 minutes, then a solution of $NaN_3$ (8.0 mg, 0.12 mmol) in $H_2O$ (1 ml) is added. The reaction mixture is stirred at 0° C. for 1 hour, during which time a yellow precipitate formed. The solid is isolated by filtration and washed with $H_2O$ and dried to afford 41.0 mg (0.083 mmol, 83%) of the desired iodoazidobiphenyl as a yellow solid. mp 173–175° C. (dec). $^1$H-NMR (DMSO) δ: 8.27, 7.98, 7.60, 7.42, 4.76, 4.16, 3.78, 3.43, 1.84.

Step 3. A mixture of 129 mg (0.26 mmol) of the iodoazidobiphenyl prepared in Step 2 (129.0 mg, 0.26 mmol), $CH_3OH$ (6 ml) and 1N HCl (2 ml) are heated at reflux for 48 hours. The cooled reaction mixture is concentrated to afford quantitative yield the desired amine hydrochloride as a tan solid. $^1$H-NMR ($CH_3OD$) δ: 7.96, 7.63, 7.46, 7.38, 7.29, 5.04, 4.34, 3.93, 3.38, 1.30.

Step 4. To a solution of 5.1 mg (0.05 mmol, 25 mCi) of tritiated acetic anhydride (Amersham Batch B77, isotope # 00–0316) is added 2 N $PCl_3$ in $CH_2Cl_2$ (25 μl). The reaction mixture is left at room temperature for 5 hours with occasional mixing. To this mixture is added a solution of the amine hydrochloride prepared in Step 3 (47.7 mg, 0.104 mmol) in pyridine (0.25 ml) followed by DMAP (4.6 mg). After 30 minutes, the reaction mixture is partitioned between $H_2O$ and $CH_2Cl_2$. The phases are separated. The aqueous phase is extracted exhaustively with $CH_2Cl_2$ and then concentrated. The residue is purified on silica gel (4 g) using 20% acetone in toluene as the eluent to afford 38.2 mg (0.077 mmol, 74%) of desired tritiated acetamide.

Example 7

Synthesis

N-[[(5S)-3-(4'-Azido-2-fluoro-3'-iodo[1,1'-biphenyl]-4-yl)-2-oxo-5-oxazolidinyl]methyl] ethane-$^{35}$S-thioamide (Compound $G_2$ of Scheme G where $R^1$ is H, $R^2$ is I, X is F, and Y is H)

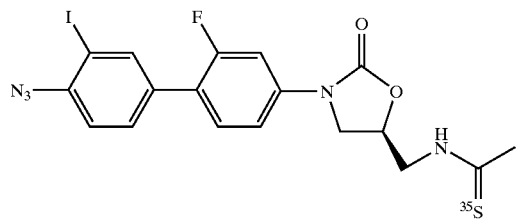

Step 1. Methylmagnesium chloride in tetrahydrofuran (THF) is treated with 35S labeled carbon disulfide at 40° C., followed by treatment with ethyl iodide. The reaction is stirred at 60° C. for 1.5 hours. After workup with water and ethyl ether, the desired ethyl $^{35}$S-dithioacetate is obtained.

Step 2. The amine hydrochloride salt prepared in Step 3 of Example 6 and the ethyl [$^{35}$S]dithioacetate prepared in Step 1 are stirred in methylene chloride, methanol, and triethylamine to give the desired $^{35}$S labeled thioamide.

Example 8

Synthesis

N-[[(5S)-3-(4'-Azido-2-fluoro-3'-iodo-$^{125}$I-[1,1'-biphenyl]-4-yl)-2-oxo-5-oxazolidinyl]methyl] acetamide (Compound $H_3$ of Scheme H where X is F, Y is H, Q is oxazolidinone, Z is O, and $R^4$ is $CH_3$)

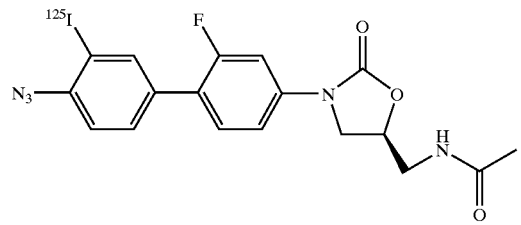

Step 1. To a stirred solution of the iodobiphenyl prepared in Step 2 of Example 6 (56.2 mg, 0.11 mmol) and hexamethylditin (73.9 mg, 0.22 mmol) in toluene (5 ml) is added palladium (II) acetate (2.6 mg, 0.011 mmol) followed by triphenylphosphine (6.5 mg, 0.022 mmol). The reaction mixture is degassed and heated at 80° C. for 20 hours. The cooled reaction mixture is concentrated to one half the volume, then purified on a Biotage 12S column using 10–20% acetone in $CH_2Cl_2$ as the eluent to afford 53.5 mg (0.10 mmol, 89%) of the desired stannane. $^1$H-NMR ($CDCl_3$) δ: 7.53, 7.43, 7.30, 7.21, 6.07, 4.83, 4.11, 3.83, 3.73, 2.05, 0.35.

Step 2. To a stirred solution of the stannane prepared in Step I in dry $CH_3CN$ and pH 7 phosphate buffer is added chloramine-T followed by a solution of 1M aqueous $Na^{125}I$. After 30 minutes, the reaction mixture is quenched with saturated aqueous $Na_2S_2O_3$ and purified to give the title compound.

Example 9

Synthesis (2E)-3-(4-Azido-3-iodo-$_{125}$I-phenyl)-N-[[(5S)-3-[3-fluoro-4-(4-pyridinyl)phenyl]-2-oxo-5-oxazolidinyl]methyl]-2-propenamide (Compound $I_4$ of Scheme I where $R^5$ is 4-pyridyl, X is F, Y is H, n is 1, $R^1$ is $^{125}$I, and $R^2$ is H)

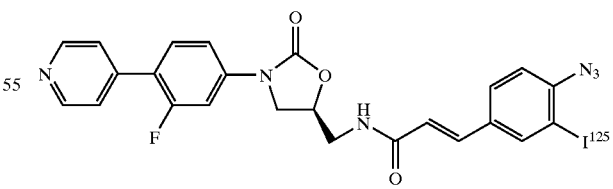

Step 1. To a stirred solution of oxalyl chloride (0.10 mL, 1.2 mmol) in $CH_2Cl_2$ (1.5 ml), cooled to -78° C., is added dry DMSO (0.14 ml, 1.97 mmol). After 10 minutes, a solution of 4-azido-3-iodobenzyl alcohol (217.0 mg, 0.79 mmol (Shu, *J. of Labeled Compounds and Radiopharmaceuticals,* 1996, 38, 227–237)) in $CH_2Cl_2$ (2.5 ml) is added. After 15 minutes, triethylamine (0.33 ml, 2.37 mmol) is added and the reaction mixture is allowed to warm to room temperature. The reaction mixture is poured into CH$_2$Cl$_2$ (30 ml) and washed successively with H$_2$O (20 ml), brine (20 ml), dried (MgSO$_4$), filtered and concentrated. The residue is purified on a Biotage 12M column using 10% EtOAC in hexane to afford 195.5 mg (0.72 mmol, 91%) of the desired aldehyde. $^1$H-NMR (CDCl$_3$) δ: 9.9, 8.31, 7.93, 7.28.

Step 2. To a stirred solution of the aldehyde prepared in Step 1 (190.0 mg, 0.69 mmol) in dry THF (1 ml) is added triethylphosphonoacetate (0.15 ml, 0.76 mmol) followed by lithium hydroxide monohydrate (32.1 mg, 0.76 mmol). The reaction mixture is stirred at room temperature for 48 hours. The reaction mixture is poured into CH$_2$Cl$_2$ (40 ml) and successively washed with H$_2$O (20 ml), brine (20 ml), dried (MgSO$_4$), filtered and concentrated. The residue is dissolved in CH$_2$Cl$_2$, absorbed onto silica gel and purified on a Biotage 40S column with a SIM using 5% EtOAC in hexane as the eluent to afford 165.1 mg (0.48 mmol, 70%) of the desired ester. mp 93–94° C. $^1$H-NMR (CDCl$_3$) δ: 7.97, 7.56, 7.16, 6.40, 4.29, 1.35.

Step 3. To a stirred solution of the ester prepared in Step 2 (66.7 mg, 0.19 mmol) in CH$_3$OH (2 ml) is added 1 N LiOH (0.19 ml, 0.19 mmol). The reaction mixture is heated at reflux for 12 hours. The cooled reaction mixture is concentrated and used immediately.

Step 4. (S)-N-[[3-[3-fluoro-4-(4-pyridyl)phenyl]-2-oxo-5-oxazolidinyl]methyl] acetamide (1.40 g, 4.25 mmol) in CH$_3$OH (62 ml) and 6 N HCl (31 ml) is heated at reflux for 18 hours. The reaction mixture is concentrated to afford 1.48 g of the amine bis-hydrochloride salt. $^1$H-NMR (DMSO) δ: 8.98, 8.62, 8.26, 7.75, 7.56, 7.35, 5.76, 5.07, 4.28, 4.30, 3.27.

Step 5. The amine bis-hydrochloride (from Step 4) (68.2 mg, 0.19 mmol), the lithium carboxylate prepared in Step 3, 1-[3-(dimethylamino)propyl]-3-ethylcarbodiimide hydrochloride (72.8 mg, 0.38 mmol) and 1-hydroxybenzotriazole hydrate (30.8 mg, 0.23 mmol) are dissolved in pyridine (2 ml) and stirred at room temperature for 72 hours. The reaction mixture is concentrated. The residue is dissolved in CH$_2$Cl$_2$ (40 ml) and washed with H$_2$O (20 ml), brine (20 ml), dried (MgSO$_4$), filtered and concentrated. The residue is dissolved in CH$_3$OH/CH$_2$Cl$_2$, absorbed onto silica gel and is purified on a Biotage 12M column with SIM using 2% CH$_3$OH (saturated with NH$_3$) in CH$_2$Cl$_2$ as the eluent to afford 56.2 mg (0.096 mmol, 51%) of the desired cinnamide. $^1$H-NMR (DMSO) δ: 8.66, 8.48, 8.02, 7.64, 7.49, 7.40, 7.35, 6.70, 4.86, 4.22, 3.84, 3.60.

Step 6. To a stirred solution of the iodocinnamide prepared in Step 4 and hexamethylditin in dry THF is added tetrakis(triphenylphosphine)palladium(0). The reaction mixture is degassed and heated at reflux for 12 hours. The cooled reaction mixture is filtered through a plug of celite and the filtrate is absorbed onto silica gel and purified on a Biotage 12M column with SIM to afford the stannane.

Step 7. To a stirred solution of the stannane prepared in Step 5 in dry acetonitrile is added a solution of 1M aqueous Na$^{125}$I followed by chloramine-T hydrate. After stirring at room temperature for 30 minutes, the reaction mixture is quenched with saturated aqueous Na$_2$S$_2$O$_3$ and purified to give the desired radioiodinated material.

Example 10

Synthesis

4-Azido-N-[[(5S)-3-[3-fluoro-4-(4-pyridinyl)phenyl]-2-oxo-5-oxazolidinyl]methyl]-2-hydroxy-5-iodo-$^{125}$I-benzamide (Compound J$_2$ of Scheme J where R$^5$ is 4-pyridyl, X is F, and Y is H, and n is 0)

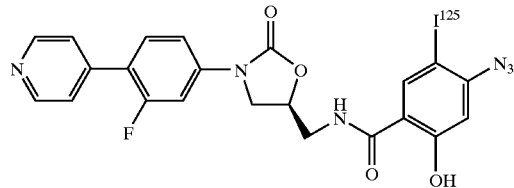

Step 1. To a stirred suspension of the amine bis-hydrochloride salt prepared in Step 4 of Example 9 (172.4 mg, 0.48 mmol) in pyridine (4 ml) and CH$_2$Cl$_2$ (1 ml) is added 4-azidosalicylic acid (128.9 mg 0.72 mmol) followed by added 1-[3-(dimethylamino)propyl]-3-ethylcarbodiimide hydrochloride (184.0 mg, 0.96 mmol) and 1-hydroxybenzotriazole hydrate (77.8 mg, 0.58 mmol). The reaction mixture is stirred at room temperature for 72 hours then concentrated. The residue is dissolved in CH$_3$OH/CH$_2$Cl$_2$, absorbed onto silica gel and purified on a Biotage 40S column with SIM using EtOAC as the eluent to afford 44.8 mg (0.10 mmol, 21%) of the benzamide as a tan solid. mp 200–202° C. (dec). $^1$H-NMR (DMSO) δ: 12.5, 9.1, 8.66, 7.92, 7.70, 7.67, 7.61, 7.50, 7.46, 6.70, 6.60, 4.93, 4.25, 3.92, 3.70.

Step 2. Starting with the phenol prepared in Step 1, $^{125}$I is introduced according to the procedure described in Step 2 of Example 1.

Example 11

Synthesis

N-(4-Azidophenyl)-N'-[[(5 S)-3-[3-fluoro-4-(4-pyridinyl)phenyl]-2-oxo-5-oxazolidinyl]methyl]-$^{35}$S-thiourea (Compound L$_3$ of Scheme L where R$^5$ is 4-pyridyl, X is F, Y is H, R$^1$ is H and R$^2$ is H)

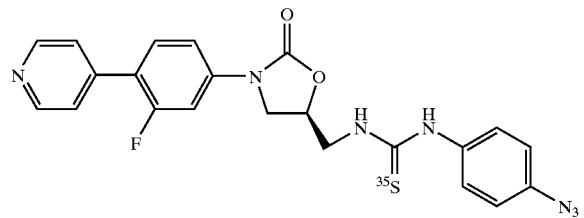

To a stirred solution of the amine bis-hydrochloride (from Step 4 of Example 9) in dry THF is added Hunig's base followed by $^{35}$S-4-azidophenylisothiocyanate in THF. The reaction mixture is heated at reflux for 1 hour. The cooled reaction mixture is cooled and purified to give the desired thiourea.

As those skilled in the art will appreciate, numerous changes and modifications may be made to the preferred embodiments of the invention without departing from the spirit of the invention. It is intended that all such variations fall within the scope of the invention. The entire disclosure of each publication cited herein is hereby incorporated by reference.

What is claimed is:
1. A compound comprising the formula

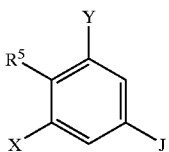

wherein:

X and Y are, independently, F, H or $CH_3$;

$R^5$ is

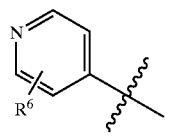 or 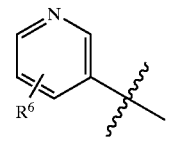

wherein:

$R^6$ is H, $N_3$, halogen, $NH_2$, OH, SH, $C_1$–$C_4$ alkylamino, $C_1$–$C_4$ dialkylamino, $C_1$–$C_4$ alkyl, nitrile, carboxamide, $C_1$–$C_4$ alkoxy, $C_1$–$C_4$ alkylthio, or $C_1$–$C_4$ alkoxycarbonyl; and J is

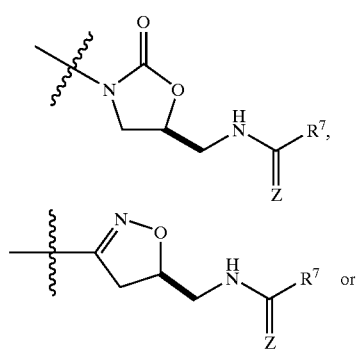

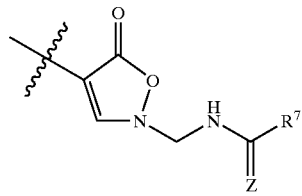

wherein:

Z is O or S; and $R^7$ is

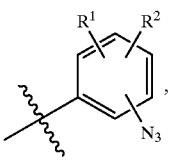, 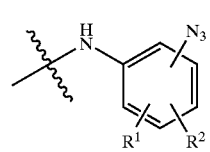 or

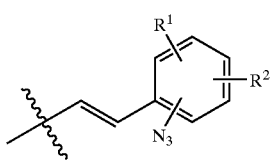

wherein:

$R^1$ is H or I; and $R^2$ is H or OH;

or a pharmaceutically acceptable salt or isotopic form thereof.

2. A compound of claim 1 wherein X is F, Y is H, and $R^6$ is H.

3. A compound of claim 1 wherein said compound is (2E)-3-(4-azido-3-iodo-$^{125}$I-phenyl)-N-[[(5S)-3-[3-fluoro-4-(4-pyridinyl)phenyl]-2-oxo-5-oxazolidinyl]methyl]-2-propenamide.

4. A compound of claim 1 wherein said compound is 4-azido-N-[[(5S)-3-[3-fluoro-4-(4-pyridinyl)phenyl]-2-oxo-5-oxazolidinyl]methyl]-2-hydroxy-5-iodo-$^{125}$I-benzamide.

5. A compound of claim 1 wherein said compound is N-(4-azidophenyl)-N'-[[(5S)-3-[3-fluoro-4-(4-pyridinyl)phenyl]-2-oxo-5-oxazolidinyl]methyl]-$^{35}$S-thiourea.

* * * * *